(12) United States Patent
Liu et al.

(10) Patent No.: US 8,901,131 B2
(45) Date of Patent: Dec. 2, 2014

(54) GATIFLOXACIN-CONTAINING OPHTHALMIC GEL AND PREPARATION METHOD THEREOF

(75) Inventors: Jidong Liu, Liaoning (CN); Yuchun Yang, Liaoning (CN); Hai Tang, Liaoning (CN)

(73) Assignee: Shenyang Xingqi Pharmaceutical Co., Ltd., Liaoning (CN)

( * ) Notice: Subject to any disclaimer, the term of this patent is extended or adjusted under 35 U.S.C. 154(b) by 0 days.

(21) Appl. No.: 13/581,415

(22) PCT Filed: Nov. 23, 2010

(86) PCT No.: PCT/CN2010/001880
§ 371 (c)(1),
(2), (4) Date: Aug. 27, 2012

(87) PCT Pub. No.: WO2011/063606
PCT Pub. Date: Jun. 3, 2011

(65) Prior Publication Data
US 2013/0040960 A1    Feb. 14, 2013

(30) Foreign Application Priority Data

Nov. 27, 2009 (CN) .......................... 2009 1 0178399

(51) Int. Cl.
A61K 31/496 (2006.01)
A61K 9/00 (2006.01)
A61K 47/32 (2006.01)
A61K 47/36 (2006.01)

(52) U.S. Cl.
CPC ............. *A61K 31/496* (2013.01); *A61K 9/0048* (2013.01); *A61K 47/32* (2013.01); *A61K 47/36* (2013.01)
USPC ..................................................... 514/253.08

(58) Field of Classification Search
USPC ..................................................... 514/253.08
See application file for complete search history.

(56) References Cited

FOREIGN PATENT DOCUMENTS

| CN | 1397272 A | 2/2003 |
|---|---|---|
| CN | 1562030 A | 1/2005 |
| CN | 1562033 A | 1/2005 |

OTHER PUBLICATIONS

International Preliminary Report on Patentability mailed May 30, 2012, issued in corresponding International Application No. PCT/CN2010/001880, filed Nov. 23, 2010, 6 pages.
International Search Report mailed Mar. 3, 2011, issued in corresponding International Application No. PCT/CN2010/001880, filed Nov. 23, 2010, 6 pages.

*Primary Examiner* — Zohreh Fay
(74) *Attorney, Agent, or Firm* — Christensen O'Connor Johnson Kindness PLLC

(57) ABSTRACT

An ophthalmic gel of gatifloxacin and the preparation method thereof are disclosed. The gel comprises gatifloxacin or its pharmaceutical salts, matrix and water. Said matrix is one or more selected from carbomer, mixture of carbomer and HPMC, and sodium hyaluronate.

17 Claims, 3 Drawing Sheets

US 8,901,131 B2

GATIFLOXACIN-CONTAINING OPHTHALMIC GEL AND PREPARATION METHOD THEREOF

Technical field

Figure 1:
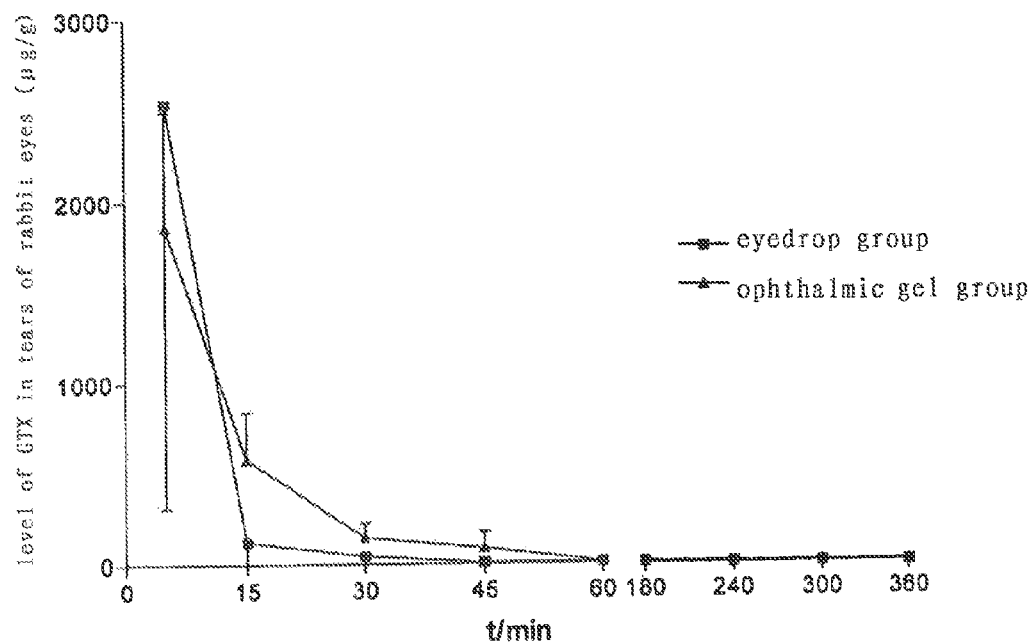

The present invention belongs to pharmaceutical formulation filed. Particularly, the present invention relates to an ophthalmic formulation, and more specifically, relates to a gatifloxacin-containing ophthalmic gel and preparation method thereof. The present invention further relates to a method for the treatment of ocular infections.

TECHNICAL BACKGROUND

Gatifloxacin belongs to fourth generation fluoroquinolone antimicrobial, and it is a broad spectrum antimicrobial which is developed by Japanese Xinlin Inc. and transferred to BMS (Bristol-Myers Squibb) Inc. In December 1999, the oral and intravenous injection formulations of the gatifloxacin are authorized by FDA to market with the trade name of Tequin. Allergan, Inc. has alleged that FDA has authorized 0.3% of ZYMAR™ (gatifloxacin eyedrops) to market in U.S.A. on March 31.

As compared with the preceding three generation quinolone drugs, the gatifloxacin mainly has the following characteristics: first of all, the gatifloxacin exhibits stronger antimicrobial activity against Gram-positive bacteria 2 to 16 times even to 32 times than the first generation to the third generation quinolone drugs; secondly, the gatifloxacin has a very strong inhibition effect on pathogenic bacteria which have tolerance to aminoglycoside, macrolide and other antibiotics, and it does not has crossed drug tolerance with these antibiotics; thirdly, the gatifloxacin has a strong activity against chlamydia, mycoplasma, etc.; at last, since the gatifloxacin introduces methoxyl groups to C8, it overcomes the side effects such as photo-toxicity; thus, the gatifloxacin is more stable in chemical structure, and its safety also is increased, The Chinese patent application No. CN1448137A (the application No. 03113340.1, the publication date is Oct. 15, 2003) discloses a gatifloxacin gel preparation for external use and eye use, which has gatifloxacin as main component and its supplementary material includes chitosan as gel substrate, iso-osmotic regulator, pH regulator, preservative, injection water, etc. The preparation has gatifloxacin content of 0.1-3 wt % and chitosan content of 0.3-3 wt %. It has obvious anti-infection function and functions of speeding heal of wound, promoting epidermal growth, inhibiting formation of scar tissue, maintaining local medicine density for long term, etc. It is used in treating burns, scalds, skin infection, folliculitis, furunculosis, pustule, trauma infections, eczema infections, gynecological vaginitis, cervicitis and ophthalmic bacillary conjunctivitis, keratitis, corneal ulcer, prevention infections and promoting wound healing after ocular operation, and virulent conjunctivitis, keratitis, aridity conjunctivitis, keratitis, and other diseases. The Chinese patent application No. CN1562030A (the application No. 200410020427.4; the publication date is Jan. 12, 2005) discloses a gatifloxacin ophthalmic gel using HPMC as matrix and the preparation method thereof, which is prepared by using gatifloxacin as active substance, hydrophilic polymer hydroxypropylmethylcellulose (HPMC) as matrix, and adding preservative, iso-osmotic regulator, osmotic regulator, pH regulator and water; the preparation method comprises the steps of dissolving gatifloxacin in water and then adding matrix, preservative, iso-osmotic regulator, osmotic regulator to the mixture with stirring to dissolve them; regulating pH=5-9 with a pH regulator; filtering the resulting solution through a microporous membrane filter, and then adding water to the filer to total volume; the formulation is suitable for treating blepharitis, hordeolum, conjunctivitis, dacryocystisis, keratitis, corneal ulcer, trachoma, and other ocular infections; it is reported that the gel formulation is a flowing semi-solid, which has the advantages of convenient usage, long residence time in eyes; the formulation does not readily run off, so as to maintain an effective treating concentration, and thus it can increase the treating effects; furthermore, the formulation has a low toxicity and stimulatory. However, the above known techniques are still required to be improved in the increase of therapeutic effects, the prolongation of residence time, the decrease of the stimulatory to eye and other aspects.

To sum up, there is still a need for providing a new gatifloxacin ophthalmic formulation, particularly ophthalmic gel, so as to overcome the defects of the existing ophthalmic gatifloxacin formulation.

SUMMARY OF THE INVENTION

The inventor has found that the gatifloxacin can be prepared into transparent carbomer ophthalmic gel with the excellent aqueous matrix carbomer, and the obtained gel can overcome the defect that the bioavailability of the conventional eyedrops is low due to the run off of drugs and the compliance of a patient is poor due to the flow of drugs into mouth through nasolacrimal duct. However, since a preservative is required to be added into the formulation, the formulation will produce stimulatory and injury to the cornea.

One object of the present invention is to prove an ophthalmic gel containing antimicrobial gatifloxacin suitable for clinical application. the inventor has surprisingly found that the combination of sodium hyaluronate and carbomer is used as matrix to prepare the gatifloxacin ophthalmic gel, which can effectively improve the properties of the formulation, for example, to reduce the topical stimulatory of the formulation to eye cornea. The present invention is achieved based on the above discovery.

For this, the first aspect of the present invention is providing an ophthalmic gel, which comprises therapeutically effective amount of gatifloxacin or its pharmaceutically acceptable salts, matrix and water, wherein the matrix is one or more selected from carbomer, mixture of carbomer and hydroxypropylmethyl cellulose (HPMC), and sodium hyaluronate. Therein, the sodium hyaluronate is combined with the above matrix to prepare gatifloxacin ophthalmic gel.

The ophthalmic gel according to any one of the first aspect of the present invention comprises therapeutically effective amount of gatifloxacin or its pharmaceutically acceptable salts, carbomer, sodium hyaluronate and water.

The ophthalmic gel according to any one of the first aspect of the present invention, in the weight/volume percentage of the gel, comprises the following components:

| | |
|---|---|
| Gatifloxacin or its pharmaceutically acceptable salts | 0.01-2.0%, |
| Carbomer | 0.01-10.0% |
| Water | q.s. to 100% |

The ophthalmic gel according to any one of the first aspect of the present invention, in the weight/volume percentage of the gel, comprises the following components:

| Gatifloxacin or its pharmaceutically acceptable salts | 0.01-2.0%, |
|---|---|
| Carbomer | 0.05-4.0% |
| Hydroxypropylmethylcellulose | 0.05-4.0% |
| Water | q.s. to 100% |

The ophthalmic gel according to any one of the first aspect of the present invention, in the weight/volume percentage of the gel, comprises the following components:

| Gatifloxacin or its pharmaceutically acceptable salts | 0.01-2.0%, |
|---|---|
| Carbomer | 0.01-10% |
| Sodium hyaluronate | 0.005-1.0% |
| Water | q.s. to 100% |

The ophthalmic gel according to any one of the first aspect of the present invention, in the weight/volume percentage of the gel, comprises the following components:

| Gatifloxacin or its pharmaceutically acceptable salts | 0.01-2.0%, |
|---|---|
| Carbomer | 0.01-2.0% |
| Sodium hyaluronate | 0.005-0.5% |
| Water | q.s. to 100% |

The ophthalmic gel according to any one of the first aspect of the present invention, in the weight/volume percentage of the gel, comprises the following components:

| Gatifloxacin or its pharmaceutically acceptable salts | 0.01-2.0%, |
|---|---|
| Carbomer | 0.1-1.0% |
| Sodium hyaluronate | 0.01-0.1% |
| Water | q.s. to 100% |

The ophthalmic gel according to any one of the first aspect of the present invention, in the weight/volume percentage of the gel, comprises the following components:

| Gatifloxacin or its pharmaceutically acceptable salts | 0.1-2.0%, |
|---|---|
| Carbomer | 0.1-1.0% |
| Sodium hyaluronate | 0.01-0.1% |
| Water | q.s. to 100% |

The ophthalmic gel according to any one of the first aspect of the present invention, in the weight/volume percentage of the gel, particularly comprises the gatifloxacin or its pharmaceutically acceptable salts in an amount of 0.1-2.0%, more particularly, 0.1-1.0%, further particularly, 0.1-0.5%, more further particularly, 0.1-0.3% or 0.1-0.2%, such as, 0.1%, 0.15%, 0.2%, 0.25%, or 0.3%.

The ophthalmic gel according to any one of the first aspect of the present invention, in the weight/volume percentage of the gel, particularly comprises the carbomer in an amount of 0.01-2.0%, more particularly, 0.1-1.0%, further particularly, 0.1-0.5%, such as, 0.1%, 0.15%, 0.2%, 0.25%, 0.3%, 0.35%, 0.4%, 0.45% or 0.5%.

The ophthalmic gel according to any one of the first aspect of the present invention, in the weight/volume percentage of the gel, particularly comprises the sodium hyaluronate in an amount of 0.005-0.5%, more particularly, 0.01-0.1%, further particularly, 0.01-0.06%, such as, 0.01%, 0.02%, 0.03%, 0.04%, 0.05%, or 0.06%.

The ophthalmic gel according to any one of the first aspect of the present invention, in the weight/volume percentage of the gel, comprises the following components:

| Gatifloxacin or its pharmaceutically acceptable salts | 0.01-2.0%, |
|---|---|
| Carbomer | 0.05-4.0% |
| Hydroxypropylmethylcellulose | 0.05-4.0% |
| Sodium hyaluronate | 0.005-1.0% |
| Water | q.s. to 100% |

The ophthalmic gel according to any one of the first aspect of the present invention further comprises a pH regulator. In one embodiment of the ophthalmic gel of the first aspect of the present invention, said pH regulator is selected from any one of boric acid, borax, sodium hydroxide, hydrochloric acid, phosphate buffered solution, acetate buffered solution or mixtures thereof. According to the present invention, the amount of the pH regulator used in a formulation will be changed due to many factors, such as, the type and strength of pH regulator, the recipe composition, the chemical and physical stabilities of drugs and formulations, etc. A person skilled in the art can understand that the amount of the pH regulator used in the gel of the present invention can be determined easily according to desirable objective pH values. For example, in the case of the desirable objective pH of 6.5-7.5, after most of materials, particularly all recipe ingredients except for water are mixed and before the volume of the formulation is determined (to final weight/volume), a suitable amount of pH regulator is used to regulate the pH of the formulation, and thus the specific amounts of the pH regulator used in the formulation can be easily determined. In one embodiment of the ophthalmic gel of the first aspect of the present invention, the pH of the ophthalmic gel is from 4.5 to 9.5, preferably from 5.5 to 8.5, more preferably from 6.0 to 8.0, even more preferably from 6.0 to 7.5.

The ophthalmic gel according to any one of the first aspect of the present invention further comprises an osmotic regulator. The examples of the osmotic regulator of the present invention include but are not limited to one of propylene glycol, glycerol, sodium chloride and mannitol etc, or mixtures thereof. According to the present invention, the amount of the osmotic regulator used in a formulation will be changed due to many factors, such as, the type and strength of the osmotic regulator, the recipe composition, the chemical and physical stabilities of drugs and formulations, etc. A person skilled in the art can understand that the amount of the osmotic regulator used in the gel of the present invention can be determined easily according to desirable objective osmotic pressure. For example, if the desirable objective osmotic pressure is basically iso-osmotic with body fluids or a little higher, after most of materials, particularly all recipe ingredients except for water are mixed, and before the volume of the formulation is determined (to final weight/volume), a suitable amount of osmotic regulator is used to regulate the osmotic pressure of the formulation, and thus the specific amounts of the osmotic regulator used in the formulation can be easily determined. In one embodiment, the ophthalmic gel of the present invention generally comprises 0-15.0% (w/v), preferably 0.01-10% (w/v), more preferably 0.01-5% (w/v), even more preferably 0.05-2% (w/v) of osmotic regulator. In addition, the amount of osmotic regulator used in a formulation can be initially determined through theoretical calculation according to existing chemical and physical knowledge. For example, in the case of sodium chloride as the osmotic regulator, the suitable concentration of sodium chloride in the formulation is 0.85-0.95% (w/v), preferably 0.88-0.92% (w/v), more preferably about 0.9% (w/v). As for amounts of other types of osmotic regulators, a person skilled in the art can easily determine them by the combination of theory and practice.

The ophthalmic gel according to any one of the first aspect of the present invention further comprises one or more bacteriostatic agents selected from the group of phenethanol, phenoxyethanol, methylparaben, ethylparaben, propylparaben, benzalkonium chloride, chlorobutanol, benzalkonium bromide, and cetrimonium bromide. In further embodiment, said bacteriostatic agent is one or more bacteriostatic agents selected from the group of phenoxyethanol, ethylparaben, benzalkonium chloride, and chlorobutanol. In more further embodiment, said bacteriostatic agent is the combination of phenoxyethanol and ethylparaben. In even further embodiment, said bacteriostatic agent is in an amount of 0.005-1% (w/v) based on the total weight of eyedrops. Preferably, said bacteriostatic agent is in an amount of 0.01-0.5% (w/v) based on the total weight of eyedrops. Preferably, said bacteriostatic agent is in an amount of 0.1-0.5% (w/v) based on the total weight of eyedrops. Preferably, said bacteriostatic agent is in an amount of 0.01-0.1% (w/v) based on the total weight of eyedrops. Preferably, said bacteriostatic agent is in an amount of 0.01, 0.1, or 0.5% (w/v) based on the total weight of eyedrops.

The ophthalmic gel according to any one of the first aspect of the present invention further comprises one or more surfactants selected from the group of tweens, polyoxyethylene hydrogenated castor oils, and polyoxyethylene castor oils, such as, but not limited to, tween-80, tween-60, tween-85, tween-65, polyoxyethylene 60 hydrogenated castor oil, etc. In one embodiment, the ophthalmic gel of the present invention comprises 0.001-10% (w/v), preferably 0.01-5% (w/v), more preferably 0.01-2% (w/v), even more preferably 0.01-1% (w/v) of the surfactants.

The second aspect of the present invention is providing an ophthalmic formulation, which comprises the ophthalmic gel according to any one of the first aspect of the present invention. The ophthalmic formulation also can be prepared into a new ophthalmic gel. Furthermore, a sodium chloride solution or a calcium chloride solution can be used to adjust the viscosity of the ophthalmic gel, so that its phase transition can be carried out in ocular physiological environment. Thus, the ophthalmic gel can acquire certain effect of clinical application.

The third aspect of the present invention is providing a preparation method for the ophthalmic gel according to any one of the first aspect of the present invention, comprising the steps of after completely swelling a polymer carbomer or carbomer and hydroxypropylcellulose and sodium hyaluronate with suitable amount of water, adding the solution of other components in water to the gel to form a gel matrix with stirring the mixture homogeneously, and bulking the homogeneous mixture.

The third aspect of the present invention provides a preparing method for the ophthalmic gel according to any one of the first aspect of the present invention, comprising the following steps:
i) swelling a polymer matrix (for example, carbomer) with suitable amount of water, dissolving and sterilizing to be ready for use; swelling a sodium hyaluronate with suitable amount of water to be ready for use;
ii) using suitable amount of water to mix with gatifloxacin and sodium hyaluronate solution, then adding an optional surfactant and an osmotic regulator to the resulting mixture to make it dissolve;
iii) dissolving an optional bacteriostatic agent and a pH regulator in water;
iv) mixing the obtained material in the item ii) with the obtained material in the item iii), then filtering the mixture through microporous membrane filter; adding the resulting filtration into the solution in the item i), and to the resulting solution, adding water to the total weight of the recipe; stirring the mixture homogeneously and then bulking the homogenous mixture to obtain desired product.

In one embodiment of the preparation method of the third aspect of the present invention, the gatifloxacin-containing ophthalmic gel can be prepared according to the following steps: a carbomer matrix is swelled with water for injection, and then let it standing for a while; the swelled matrix is sterilized at 121° C. for more than 30 minutes before the use; adjuvant materials is added to suitable amount of water for rejection to make it dissolve, and after a solubilize is hot melt, it is added to the resulting solution; an osmotic regulator is added to the mixture, and then the resulting mixture is subjected to filtration sterilization with a membrane filter (0.22 µm); the filtrate is added to gel phase; the main drug is dissolved in another suitable amount of water, and after the resulting solution is subjected to filtration sterilization with a membrane filter (0.22 µm), it is added to the gel phase with stirring homogeneously; after the ph of the mixture is adjusted, the water for rejection is added to the total weight, and the resulting mixture is stirred to become a homogeneous transparent gel.

The gatifloxacin-containing ophthalmic gel prepared according to the method of the present invention according to the method of the present invention has a clear appearance, low stimulatory, low toxicity, and thus can be a safe, effective ophthalmic formulation for clinic.

One another aspect of the present invention relates to a method for treating ocular infections, comprising the step of administering effective amount of the ophthalmic gel of the present invention; particularly, said ocular infections may be blepharitis, hordeolum, conjunctivitis, dacryocystisis, keratitis, corneal ulcer, or trachoma.

The following contents further describe respective aspects of the present invention and the advantages thereof.

As used herein, the phase "in the weight/volume percentage of the gel" means that based on 100 ml of the gel, the weight(g) of the component comprised therein is the weight/volume percentage, i.e., to be usually expressed as g/100 ml, or % (w/v). In the present invention, unless indicated otherwise, the sign % means the weight/volume percentage.

The ophthalmic gel of the present invention is an aqueous composition, wherein water is used as medium or solvent or excipient or carrier of the composition. Although as for the eyedrops of the present invention, the percentage of used water based on the total weight of the eyedrops is not specifically indicated, or when formulating the eyedrops of the present invention, the amount of used water is not specifically indicated, it is clear for a person skilled in the art that as the medium or solvent or excipient or carrier of the ophthalmic formulation, the amount of water is calculated based on that water is added to the ophthalmic gel to the total weight. This is a commonly-used calculating manner used in the process of formulating liquid formulations such as, eyedrop, liquid for injection or ophthalmic gel of the present invention.

The bacteriostatic agent comprised in the ophthalmic gel of the present invention may be any combination of one or more bacteriostatic agents. In one embodiment, said bacteriostatic agent may be the combination of phenoxyethanol and ethylparaben; in further embodiment, said bacteriostatic agent may be the combination of phenoxyethanol and ethylparaben in any ratio; in even further embodiment, said bacteriostatic agent may be the combination of phenoxyethanol and ethylparaben in the ratio of 50:1 by weight. In one embodiment, said bacteriostatic agent may be the combination of phenoxyethanol and benzalkonium chloride; in further embodiment, said bacteriostatic agent may be the combination of phenoxyethanol and benzalkonium chloride in any ratio; in even further embodiment, said bacteriostatic agent may be the combination of phenoxyethanol and benzalkonium chloride in the ratio of 50:1 by weight. In one embodiment, said bacteriostatic agent may be the combination of chlorobutanol and benzalkonium chloride; in further embodiment, said bacteriostatic agent may be the combination of chlorobutanol and benzalkonium chloride in any ratio; in even further embodiment, said bacteriostatic agent may be the combination of chlorobutanol and benzalkonium chloride in the ratio of 10:1 by weight. In one embodiment, said bacteriostatic agent may be the combination of chlorobutanol and ethylparaben; in further embodiment, said bacteriostatic agent may be the combination of chlorobutanol and ethylparaben in any ratio; in even further embodiment, said bacteriostatic agent may be the combination of chlorobutanol and ethylparaben in the ratio of 10:1 by weight.

According to the present invention, the ophthalmic gel formed by using sodium hyaluronate and carbomer as matrix is a pseudoplastic fluid, which has similar properties to tears of human, that is, when blinking, the viscosity of the formulation per se decreases rapidly, and when not blinking, the viscosity of the formulation recoveries, and thus the residence time of drugs in ocular surface is prolonged. This property renders that the ophthalmic gel of the present invention will not be "unclear" so as to influence the vision. The gel is usually a multi-dosage formulation, and thus it is necessary to add an preservative. The addition of sodium hyaluronate to the ophthalmic gel of the present invention may reduce the stimulatory and damage of the preservative on the cornea. Furthermore, the combination of sodium hyaluronate and carbomer will greatly improve the pseudoplastic feature of the gel, so that the carbomer is more easily shearing-desaturated in certain concentration.

Without be bonded to the theory, in the present invention, the combination of carbomer and sodium hyaluronate is used as the matrix of the gel, wherein the semi-solid polymer carbomer in the swelling and crosslinking state, formed after absorbing abundant water, can crosslink with sodium hyaluronate through covalent bond, hydrogen bond, van der Weals force and other manners. The carbomer can tolerate hot pressing steam sterilization, and maintains its drug delivery ratio and keeps its appearance constant. An excellent ophthalmic gel matrix prepared by the use of the combination of carbomer and sodium hyaluroate can improve its drug bioavailability and reduce the stimulatory and damage of bacteriostatic agent on corneas.

In the pharmacodynamic comparison of the gatifloxacin-containing ophthalmic gel provided by the present invention with gatifloxacin eyedrops, it can be pleasantly founded that: during the process of administering the two formulations in equivalent concentration, the level of gatifloxacin in rabbit eyes is measured; the drug concentration in rabbit eyes after administering ophthalmic gel is significantly higher than the drug concentration after administering the eyedrops in the same concentration. That is, in the case of arriving at the same treating effects, the concentration of the gatifloxacin in the ophthalmic gel provided by the present invention may be lower, and thus the object of reducing the toxic and side effects of drug is achieved.

ILLUSTRATIONS FOR THE DRAWINGS

FIG. 1: the duration of the drug in tears after the single-dose topical drug administration to rabbit eyes; (■) gatifloxacin eyedrop group, (▲) gatifloxacin ophthalmic gel group; The GTX in FIG. 1 represents gatifloxacin.

Figure 2:
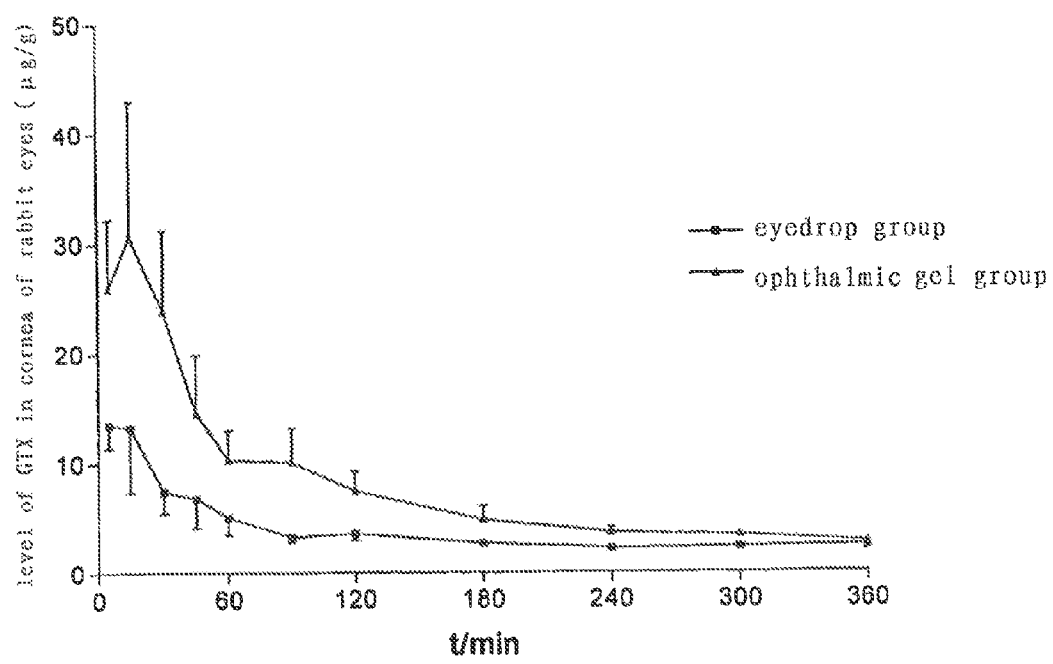

FIG. 2: the duration of the drug in corneas after the single-dose topical drug administration to rabbit eyes; (■) gatifloxacin eyedrop group, (▲) gatifloxacin ophthalmic gel group.

Figure 3:
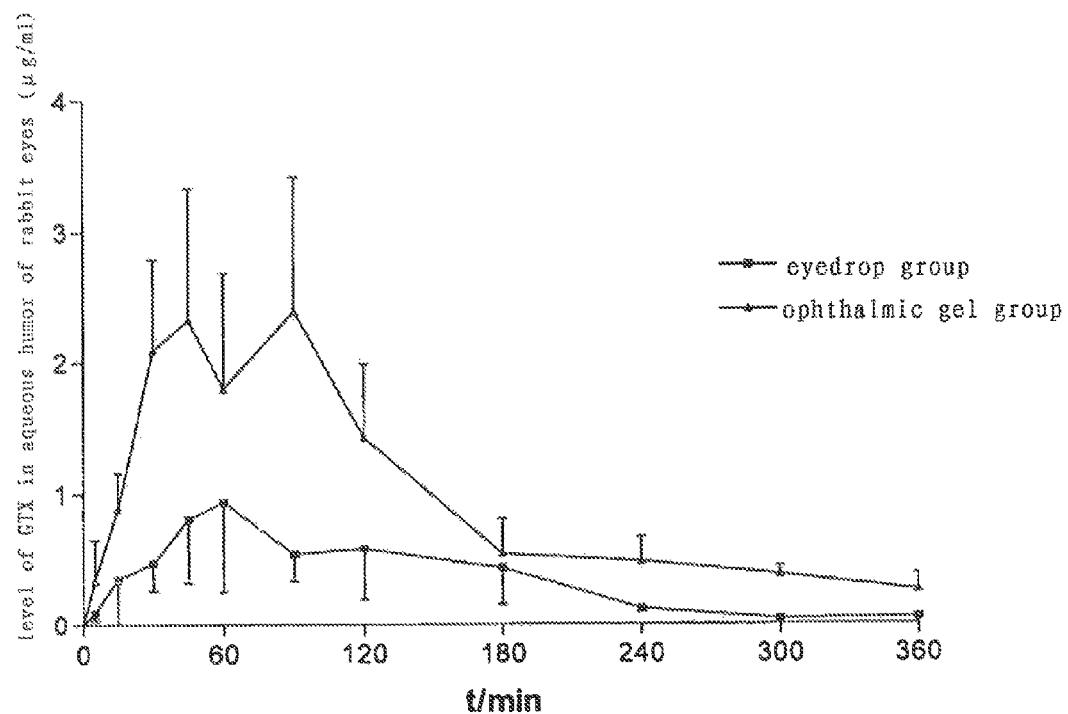

FIG. 3: the duration of the drug in aqueous humor after the single-dose topical drug administration to rabbit eyes; (■) gatifloxacin eyedrop group, (▲) gatifloxacin ophthalmic gel group.

Figure 4:
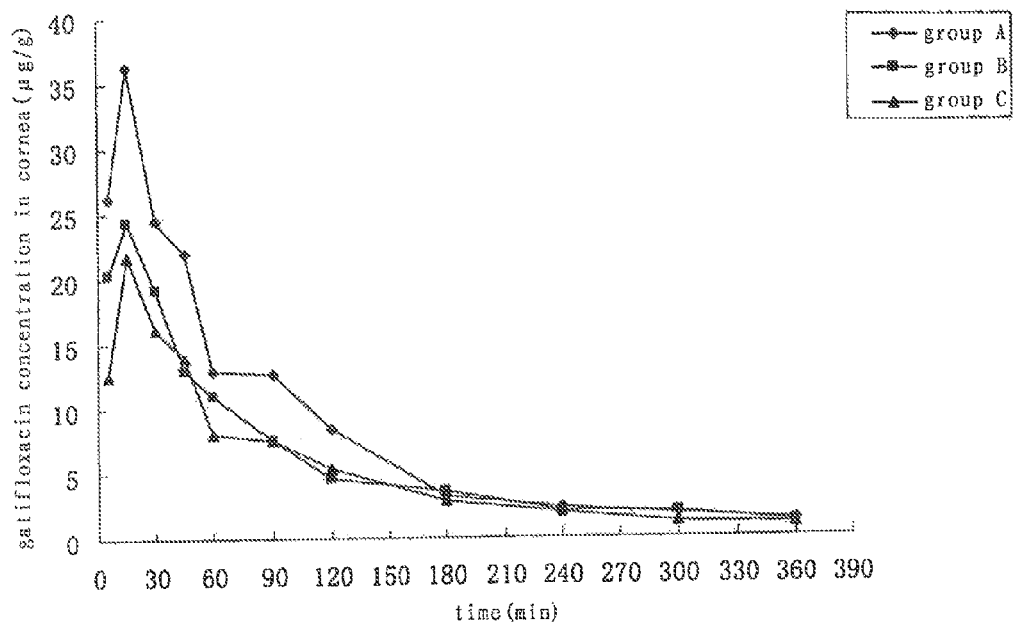

FIG. 4: the duration of the drugs in corneas of eye rabbits after single topical drug administration of three different gatifloxacin gels to rabbit eyes.

Figure 5:
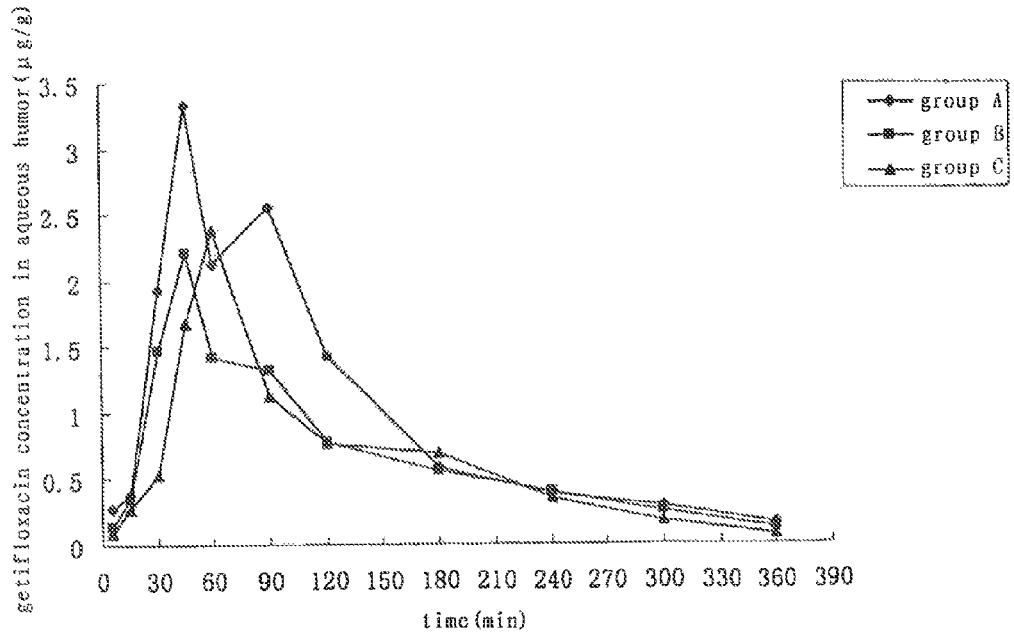

FIG. 5: the duration of the drugs in aqueous humor of eye rabbits after single topical drug administration of three different gatifloxacin gels to rabbit eyes.

PREFERRED EMBODIMENTS

The present invention is further illustrated by the following specific examples. However, the examples should be understood only to be used to illustrate the present invention in more detail, not to be used to limit the present invention in any forms.

The present invention makes general and/or specific descriptions to the materials and laboratory methods used in the experiments. Although many materials and operation methods used in order to achieve the objects of the present invention are well known in the art, the present invention still make detailed descriptions as far as possible herein. It is clear for a person skilled in the art that hereafter, the materials and operation methods of the present invention are well known in the art unless illustrated specifically.

EXAMPLE 1

Recipe:

| | |
|---|---|
| Gatifloxacin | 1.0 g |
| Carbomer | 2.0 g |
| Borax | 20.0 g |
| Glycerol | 15.6 g |
| Polyoxyethylene 60 hydrogenated castor oil | 5.0 g |
| Benzalkonium bromide | 0.2 g |
| Water for injection | supplemental to 1000 ml |

Preparation Process:

Suitable amount of water is added to the prescription amount of carbomer to swell the carbomer, and after sterilization, the solution is ready for the use; the prescription amount of benzalkonium bromide is added to suitable amount of water for injection to make it dissolve, and then the borax is added to the dissolved benzalkonium bromide solution to form a bacteriostatic agent; further, the glycerol is added to the prescription amount of polyoxyethylene 60 hydrogenated castor oil to make them miscible, and after the obtained mixture is mixed with gatifloxacin homogeneously, the homogeneous mixture is mixed with the bacteriostatic agent solution homogeneously; the resulting mixture is subjected to filtration with a membrane filter (0.22 μm) and then it is added to said carbomer solution; to the resulting mixture water for injection is supplemented to the total weight, and after the obtained solution is stirred homogeneously, it is bulked to obtain desired product.

EXAMPLE 2

Recipe:

| | |
|---|---|
| Gatifloxacin | 4.0 g |
| Carbomer | 3.0 g |
| Hydroxypropylmethylcellulose | 2.0 g |
| Boric acid | 20.0 g |
| Glycerol | 15.6 g |
| tween | 5.0 g |
| Benzalkonium bromide | 0.2 g |
| Water for injection | supplemental to 1000 ml |

Preparation Process:

Suitable amount of water is added to the prescription amount of carbomer and hydroxypropylmethycellulose to swell them, and after sterilization, the solution is ready for the use; the prescription amount of benzalkonium bromide is added to suitable amount of water for injection to make it dissolve, and then the boric acid is added to the dissolved benzalkonium bromide solution to form a bacteriostatic agent solution; further, the glycerol is added to the prescription amount of tween to make them miscible, and after the obtained mixture is mixed with gatifloxacin homogeneously, the homogeneous mixture is mixed with the bacteriostatic agent solution homogeneously; the resulting mixture is subjected to filtration with a membrane filter (0.22 μm) and then it is added to said carbomer solution; to the resulting mixture water for injection is supplemented to the total weight, and after the obtained solution is stirred homogeneously, it is bulked to obtain desired product.

EXAMPLE 3

Recipe:

| | |
|---|---|
| Gatifloxacin | 4.0 g |
| Carbomer | 3.0 g |
| Sodium hyaluronate | 0.1 g |
| Hydroxypropylmethylcellulose | 2.0 g |
| Sodium hydroxide | 8.0 g |
| Glycerol | 15.6 g |
| tween | 5.0 g |
| Ethylparaben | 0.2 g |
| Water for injection | supplemental to 1000 ml |

Preparation Process:

Suitable amount of water is added to the prescription amount of carbomer and hydroxypropylmethycellulose to swell them, and after sterilization, the solution is ready for the use; suitable amount of water for injection is added to the sodium hyaluronate to swell it to be ready for the use; the prescription amount of ethylparaben is added to suitable amount of water for injection to make it dissolve, and then the sodium hydroxide is added to the dissolved ethylparaben solution to form a bacteriostatic agent; further, the glycerol is added to the prescription amount of tween to make them miscible, and after the obtained mixture is mixed with gatifloxacin and sodium hyaluronate solution homogeneously, the homogeneous mixture is mixed with the bacteriostatic agent solution homogeneously; the resulting mixture is subjected to filtration with a membrane filter (0.22 μm) and then it is added to said carbomer solution; to the resulting mixture water for injection is supplemented to the total weight, and after the obtained solution is stirred homogeneously, it is bulked to obtain desired product.

EXAMPLE 4

Recipe:

| | |
|---|---|
| Gatifloxacin | 3.0 g |
| Carbomer | 4.0 g |
| Calcium chloride | 0.30 g |
| Sodium hyaluronate | 0.2 g |
| Sodium hydroxide | 8.0 g |
| Propylene glycol | 16.0 g |
| Ethylparaben | 0.2 g |
| Water for injection | supplemental to 1000 ml |

Preparation Process:

Suitable amount of water is added to the prescription amount of carbomer to swell it, and after sterilization, the solution is ready for the use; the sodium hyaluronate is mixed with suitable amount of water for injection to swell it to be ready for the use; after the calcium chloride is dissolved by suitable amount of water for injection, the solution is mixed with the prescription amount of ethylparaben to make it dissolve, and then the sodium hydroxide is added to the dissolved ethylparaben solution to form a bacteriostatic agent; further, the prescription amount of propylene glycol is mixed with gatifloxacin and the sodium hyaluronate solution to make them miscible, and the homogeneous mixture is mixed with the bacteriostatic agent solution homogeneously; the resulting mixture is subjected to filtration with a membrane filter (0.22 μm) and then it is added to said carbomer solution; to the resulting mixture water for injection is supplemented to the total weight, and after the obtained solution is stirred homogeneously, it is bulked to obtain desired product.

EXAMPLE 5

Recipe:

| | |
|---|---|
| Gatifloxacin | 3.0 g |
| Carbomer | 3.5 g |
| Sodium hyaluronate | 0.6 g |
| Borax | 9.0 g |
| Propylene glycol | 11.0 g |
| Ethylparaben | 0.2 g |
| Water for injection | supplemental to 1000 ml |

Preparation Process:

Suitable amount of water is added to the prescription amount of carbomer to swell it, and after sterilization, the solution is ready for the use; sodium hyaluronate is mixed with suitable amount of water for injection to swell it to be ready for the use; the prescription amount of ethylparaben is added to suitable amount of water for injection to make it dissolve, and then the borax is added to the dissolved ethylparaben solution to form a bacteriostatic agent; further, the prescription amount of propylene glycol is mixed with the gatifloxacin and the sodium hyaluronate solution to make them miscible, and the homogeneous mixture is mixed with the bacteriostatic agent solution homogeneously; the resulting mixture is subjected to filtration with a membrane filter (0.22 μm) and then it is added to said carbomer solution; to the resulting mixture water for injection is supplemented to the total weight, and after the obtained solution is stirred homogeneously, it is bulked to obtain desired product.

EXAMPLE 6

Recipe:

| | |
|---|---|
| Gatifloxacin | 1.0 g |
| Carbomer | 2.0 g |
| Sodium hyaluronate | 0.5 g |
| Borax | 20.0 g |
| Propylene glycol | 15.6 g |
| Ethylparaben | 0.3 g |
| Water for injection | supplemental to 1000 ml |

Preparation Process:

Suitable amount of water for injection is added to the prescription amount of carbomer to swell it, and after sterilization, the solution is ready for the use; the sodium hyaluronate is added to suitable amount of water for injection to swell it to be ready for the use; the prescription amount of ethylparaben is added to suitable amount of water for injection to make it dissolve, and then the borax is added to the dissolved ethylparaben solution to form a bacteriostatic agent; further, the prescription amount of propylene glycol is mixed with the gatifloxacin and sodium hyaluronate solution to make them miscible, and the homogeneous mixture is mixed with the bacteriostatic agent solution homogeneously; the resulting mixture is subjected to filtration with a membrane filter (0.22 μm) and then it is added to said carbomer solution; to the resulting mixture water for injection is supplemented to the total weight, and after the obtained solution is stirred homogeneously, it is bulked to obtain desired product.

EXAMPLE 7

Recipe:

| | |
|---|---|
| Gatifloxacin | 0.5 g |
| Carbomer | 1 g |
| Sodium hyaluronate | 0.1 g |
| Ethylparaben | 0.01 g |
| propylparaben | 0.02 g |
| Sodium chloride | 0.9 g |
| Tween-80 | 0.5 g |
| Borax | suitable amount to adjust pH to about 7.0 |
| Water for injection | suitable amount to supplement to 1000 ml |

Preparation Process:

Suitable amount of water for injection is added to the prescription amount of carbomer to swell it, and after sterilization, the solution is ready for the use; sodium hyaluronate is mixed with suitable amount of water for injection to swell it to be ready for the use; the prescription amount of ethylparaben and propylparaben are added to suitable amount of water for injection to make them dissolve, and then the borax is added to the dissolved solution to form a bacteriostatic agent; further, the prescription amount of sodium chloride, gatifloxacin, sodium hyaluronate solution and tween are mixed with suitable amount of water to make them miscible, and the homogeneous mixture is mixed with the bacteriostatic agent solution homogeneously; the resulting mixture is subjected to filtration with a membrane filter (0.22 μm) and then it is added to said carbomer solution; the pH of the obtained mixture is adjusted to about 7.0 by using suitable amount of boric acid (if necessary, suitable amount of sodium hydroxide is applicable), and to the resulting mixture water for injection is supplemented to the total weight; after the obtained solution is stirred homogeneously, it is bulked to obtain desired product.

A person skilled in the art can understand that although the weight unit of respective components in Examples 1-7 is gram, it can also be understood as weight part, that is, respective components only is required to meet the ratio of the components in the recipes of Examples 1-7.

COMPARATIVE EXAMPLE 1

Recipe:

| | |
|---|---|
| Gatifloxacin | 3 g |
| Propylene glycol | 90 g |
| Glycerol | 100 g |
| Carbomer | 10 g |
| triethanolamine | 15 g |
| Water for injection | suitable amount to supplement to 1000 ml |

Preparation Process:

Suitable amount of water for injection is added to the prescription amount of carbomer and glycerol, with stirring them homogeneously, and swelling them to form a gel matrix to be ready for the use; suitable amount of water for injection is added to the prescription amount of triethanolamine with stirring them homogeneously to be ready for the use; suitable amount of water for injection is added to the prescription amount of gatifloxacin with stirring them homogeneously, and then the propylene glycol is added thereto; the above three solutions are mixed, then filtered with 0.22 micron membrane filter; following this, water for injection is supplemented to the total weight, and after the obtained solution is stirred homogeneously, it is bulked to obtain desired product.

COMPARATIVE EXAMPLE 2

Recipe:

| | |
|---|---|
| Gatifloxacin | 3 g |
| Sodium hyaluronate | 2.5 g |
| Benzalkonium Chloride | 0.01 g |
| Sodium chloride | 1.5 g |
| Hydroxypropyl-β-cyclodextrin | 3.5 g |
| Boric acid | adjust pH to 7 |
| Water for injection | supplement to 1000 ml |

Preparation Process:

Suitable amount of water for injection is added to the prescription amount of gatifloxacin with stirring them homogeneously to dissolve them; the prescription amount of sodium hyaluronate is added to the above solution to swell; then, the prescription amount of benzalkonium chloride, sodium chloride and hydroxypropyl-β-cyclodextrin are added thereto in turn, and the obtained solution is stirred homogeneously; the pH of the solution is adjusted to 7 with boric acid, and then it is filtered through a membrane filter (0.22 μm); following this, water for injection is supplemented to the total weight, and after the obtained solution is stirred homogeneously, it is bulked to obtain a sample solution.

TEST EXAMPLE 1

Assay for Stimulatory to Eyes

I. Materials
1. Tested Drugs:

Administration group: The ophthalmic gel of gatifloxacin prepared in Example 5 Comparative group: The blank sample prepared by removing gatifloxacin according to Example 5.

2. Animal

Rabbit, Japanese white rabbits, each having a weight of about 2.6 to 3.0 kg, male and female both, provided by Animal research institute of Shuangyi of Shenyang City.

II. Test Procedure and Results
1. Eye Stimulation Experiment of Single Administration Test procedure: four New Zealand rabbits are taken, and both eyes of each one are checked in 24 hours before the experiment. The animals which take eye stimulation symptom, cornea defects and conjunctiva damages can not be used in the experiment. Eye lash of each animal is cut off. One drop of gatifloxacin ophthalmic gel is administered to the conjunctival sac of right eye of each animal, and equivalent mount of blank sample is administered to the left eye as a control. On each administration, nasolacrimal canal is oppressed, and after the administration, the eyes of rabbit are forced to close for 10 seconds. Following this, 2% of fluorescein sodium is administered to rabbit eyes dropwise by instillation, and then the topical stimulation reaction in 1, 2, 4, 24, 48, 72 hours after the administration are observed with slit lamp. According to score standards (Table 1), the cornea, iris, and conjunctiva are scored respectively, and the average values are calculated. Then, the administration group and the comparative group are compared to evaluate the eye stimulatory of the drugs according to the standards shown in Table 2. The test results are shown in Table 3.

TABLE 1

Scores of eye stimulation reaction

| Eye stimulation reaction | score |
|---|---|
| Corneaeopacitas (based on the most compact parts) | |
| Noopacitas | 0 |
| Scattering or diffusingopacitas, clear iris, | 1 |
| Translucent area is readily identified, vague iris | 2 |
| Gray transparent area appears, the details of the iris are unclear, and the size of the pupil is barely saw. | 3 |
| Opaque cornea, and due to the opacitas, the iris can not be identified | 4 |
| iris | |
| normal | 0 |
| The crease is deepened obviously, congested, swollen, the periphery of the cornea is slightly congested, and the pupil is still reactive to light. | 1 |
| Bleeding, necrosis with naked eyes, unreactive to light (or one of reactions therein) | 2 |
| Conjunctiva | |
| A. congested (as for palpebral conjunctiva, bulbar conjunctiva parts) | |
| Normal blood vessels | 0 |
| Blood vessels are congested and appeared red | 1 |
| Blood vessels are congested and appeared red, and they can not be easily identified | 2 |

TABLE 1-continued

Scores of eye stimulation reaction

| Eye stimulation reaction | score |
|---|---|
| Blood vessels are diffusingly congested, and appeared prunosus | 3 |
| B. hydrops | |
| No hydrops | 0 |
| Slight hydrops (including nictitating membrane) | 1 |
| Obvious hydrops, accompanying partial ectropion | 2 |
| Hydrops to eyelid, near to semi-closed | 3 |
| Hydrops to eyelid, surpassing semi-closed | 4 |
| C. secretions | |
| No secretions | 0 |
| A little of secretions | 1 |
| Secretions make the eyelid and eyelash moisture or adhering | 2 |
| Secretions make the whole eye area moisture or adhering | 3 |
| Total scores | 16 |

TABLE 2

Evaluation standards of eye stimulations

| Stimulatory | scores |
|---|---|
| No stimulatory | 0-3 |
| Light stimulatory | 4-8 |
| Medium stimulatory | 9-12 |
| Strong stimulatory | 13-16 |

TABLE 3

Results of eye stimulation experiment of single administration ($X \pm SD$)

| Group | The number of animals (n) | Scores of stimulation |
|---|---|---|
| Comparative group | 4 | 0 |
| Administration group | 4 | 0.5 |

The test results show that single administration of the present product does not have stimulatory to rabbit eyes.

2. Observation for the Stimulatory of Multiple Administrations to Rabbit Eyes

Test procedure: four New Zealand rabbits are taken, and both eyes of each one are checked in 24 hours before the experimental. The animals which take eye stimulation symptom, cornea defects and conjunctiva damages can not be used in the experiment. The administration method and dosage are the same as the single administration. The rabbit is administered six times one day, and administered for continuous 7 days. Every day, the topical stimulation reactions in 1, 2, 4, 24, 48, 72 hours before the administration and after the last administration are observed with slit lamp. According to score standards (Table 1), the cornea, iris, and conjunctiva are scored respectively, and the average values are calculated. Then, the administration group and the comparative group are compared to evaluate the eye stimulatory of the drugs according to the standards shown in Table 2. The test results are shown in Table 4.

TABLE 4

Results of eye stimulation experiment of multiple administration (X(SD)

| Group | The number of animals (n) | Scores of stimulation |
|---|---|---|
| Comparative group | 4 | 0 |
| Administration group | 4 | 0 |

The results show that after each administration, the rabbit eyes are normal. The score result: the comprehensive score of eye stimulation is zero, and this shows that the ophthalmic gel of gatifloxacin does not have stimulatory to rabbit eyes through multiple administration.

III. Conclusion:

The results show that: in respective animals of administration group, after administration, the obvious stimulation of drug subjected to animal subjects is not found in respective time points; in respective animals of comparative group, after administering an excipient, the obvious stimulation of drug subjected to animal subjects is not found in respective time points; the evaluation to eye stimulation is no stimulatory; in respective animals of respective group, dysphoria, hypersomnia and other abnormal behaviors are not observed during the administration and observation.

TEST EXAMPLE 2

Study on Bioavailability in Rabbit Eye of Gatifloxacin Ophthalmic Gel

After single administration to rabbit eyes, the concentrations of gatifloxacin ophthalmic gel in tears, cornea and aqueous humor are measured at different time points, and by comparing the concentrations with the single administration of gatifloxacin eyedrops in rabbit eyes at corresponding time points, their ocular relative bioavailabilities are compared.

1. Materials 1.1 Main Reagents

Acetonitrile (HPLC grade, batch number: 509124, TEDIA Inc. U.S.A.); methanol (HPLC grade, batch number: UN1230, Merck Inc. German); dichloromethane (chromatographic purity, Kemiou Chemical Reagent research institute of Tianjin). gatifloxacin control sample (the content of 97.2%, China Biological Article Standardization Institute).

1.2 Test Drug

Gatifloxacin ophthalmic gel prepared according to the process of Example 5 (GTX-Gel)

1.3 Comparative Drug

Market-available gatifloxacin eyedrops (GTX-ED, specification: 0.3%)

1.4 Animals and Grouping

Male Japanese white rabbits each is health, without ocular diseases, and has a weight of about 2 to 2.5 kg (provided by Laboratory Animal Center of Henan Province, Certification No: SCXK(Yu)2005-0002). They are completely randomly grouped into a test group and a comparative group, and each group includes 44 animals. The animals in each group are grouped into 11 subgroups, and each subgroup includes 4 animals with 8 eyes.

1.5 Administration and Sampling

Test group (gel group): 0.050 g of gatifloxacin ophthalmic gel are accurately weighed by using clear glass eyedrop rod, and it is softly administrated to the bitamporal of conjunctival sac in the lower eyelid of the rabbit once. Then, the two eyelids are closed softly for about 30 seconds;

Comparative group (eyedrop group): 50 µl of gatifloxacin eyedrops are respectively administered to the conjunctival sac of two eyes of rabbits by using a micro-sampler, and then the two eyelids are closed softly for about 30 seconds.

For each group, at 5, 15, 30, 45, 60, 90, 120, 180, 240, 300 and 360 minutes after administration, a filter paper strip which has been peeled in a glass test tube is placed in the conjunctival sac for 10 seconds, and then it is taken out to accurately weigh the weight of tears at once. A polydocanol is administered to eyes dropwise, and then a 1 ml syringe with a 26 gage injection needle is used to quickly stick into anterior chamber through the upper edge of the cornea to draw aqueous humor off; 100 µl of aqueous humor is imbibed accurately to place into a centrifugation test tube with a stopple. Rabbits were sacrificed by excessive administration of pentobarbital sodium at the edge of ears, and the cornea tissues thereof are dissected out. The moisture of the obtained cornea tissue is blotted up with filter paper, and then the tissue is placed in a glass test tube to accurately weigh the weight thereof. All the samples are stored in a freezer at −60° C., and before the use, the frozen samples are thawed by returning the temperature to room temperature to be ready for treatment and determination.

1.6 Treatments to Samples

Tears: a mobile phase is added into the test tube containing the filter paper strip with tears, followed by shaking (at 4500 rpm for 1 minute) and centrifugal separation (for 15 minutes), and then the supernatant is separated and infused into a liquid chromatograph.

Aqueous humor: 100 µl of aqueous humor is accurately imbibed, and then 2.0 ml of dichloromethane is added, followed by swirl shaking (for 1 minute) and centrifugal separation (at 3000 rpm for 5 minutes). The upper aqueous layer is discarded, and the organic layer is collected. The obtained organic layer is blown dried with nitrogen gas by heating at 40° C. Before measurement, a mobile phase is added to the dried organic layer with swirl shaking (at 4500 rpm for 1 minute) and centrifugal separation (for 15 minutes). The supernatant is separated to infuse into a high pressure liquid chromatograph. By the calculation of external standard method of peak area, the concentration of the sample can be obtained.

Cornea sample: the accurately weighed cornea is chopped and then placed into a test tube, and then 1.0 ml of water is added. The mixture is homogenized by a tissue homogenizer (Fluko, German, at 25000 rpm for 1 minute). 200 µl of cornea homogenates are mixed with 2.0 ml of dichloromethane, and the other treating methods are the same as the treating methods for aqueous humor sample.

1.7 Determination for samples: the tears, aqueous humor and cornea samples are respectively treated according to the methods in "the treatment to samples" item. The supernatant is separated to infuse into a high pressure liquid chromatograph, and the chromatogram and peak area are recorded. The concentrations of drugs in tears, aqueous humor and cornea samples are calculated by quantitation of external standard method.

2. Results 2.1 Pharmacokinetic Analysis and Ocular Relative Bioavailability in Rabbit Eyes of Gatifloxacin Ophthalmic Gel and Gatifloxacin Eyedrops 2.1.1 Duration of Gatifloxacin Ophthalmic Gel and Gatifloxacin Eyedrops in Rabbit Eyes The results of the drug concentration of gatifloxacin ophthalmic gel and gatifloxacin eyedrops in tears after single administration are shown in Table 5 and FIG. 1. The drug concentrations of the gatifloxacin ophthalmic gel group in tears respectively are 581.83±261.19, 147.46±79.84 and 87.07±88.87 μg/g at 15, 30 and 45 minute after administration, and respectively are 2.5, 3.4 and 10.7 times of the gatifloxacin eyedrop group at corresponding time points. The drug concentrations of the gatifloxacin ophthalmic gel group in tears at respective time point of from 15 to 45 minute are made a t-test over the gatifloxacin eyedrop group, and the results have significant differences (p<0.05). The area under the drug concentration in tears-time curve at the time of from 0 to 360 minute after administration is as follow: AUCGTX-Gel/AUCGTX-ED=1.2.

minute after administration, which is 0.94±0.6911 g/ml. The drug concentration of the gatifloxacin ophthalmic gel in aqueous humor is sustained a relatively high drug concentration at the time of from 5 to 120 minute after administration, and are respectively 3.8, 2.5, 4.4, 2.9, 1.9, 4.4 and 2.5 times of the gatifloxacin eyedrop group at the corresponding time points. The drug concentrations of the gatifloxacin ophthalmic gel group in aqueous humor at respective time point of from 5 to 360 minute except for 180 minute are made a t-test over the gatifloxacin eyedrop group, and the results have significant differences (p<0.05). The area under the drug concentration

TABLE 5

Concentration of gatifloxacin in tears, cornea and aqueous humor of rabbit eyes

| | Drug concentration in tears | | Drug concentration in cornea | | Drug concentration in aqueous humor | |
|---|---|---|---|---|---|---|
| time (min) | Eye drop group (μg/ml) ($\bar{x} \pm s$) | Gel group (μg/ml) ($\bar{x} \pm s$) | Eye drop group (μg/ml) ($\bar{x} \pm s$) | gel group (μg/ml) ($\bar{x} \pm s$) | Eye drop group (μg/ml) ($\bar{x} \pm s$) | Gel group (μg/ml) ($\bar{x} \pm s$) |
| 5 | 2543.11 ± 2231.39 | 1864.85 ± 636.70 | 13.56 ± 2.16 | 25.91 ± 6.30** | 0.09 ± 0.06 | 0.34 ± 0.31* |
| 15 | 124.17 ± 127.52 | 581.63 ± 261.19** | 13.29 ± 5.92 | 30.63 ± 12.32** | 0.35 ± 0.44 | 0.89 ± 0.27* |
| 30 | 43.95 ± 55.22 | 147.46 ± 79.85** | 7.46 ± 2.05 | 23.87 ± 7.37** | 0.47 ± 0.21 | 2.09 ± 0.70** |
| 45 | 8.12 ± 3.11 | 87.07 ± 88.87* | 6.80 ± 2.74 | 14.53 ± 5.31** | 0.81 ± 0.49 | 2.33 ± 1.01** |
| 60 | 9.31 ± 9.50 | 10.53 ± 6.09 | 5.04 ± 1.62 | 10.25 ± 2.69** | 0.94 ± 0.69 | 1.80 ± 0.89* |
| 90 | 3.00 ± 2.82 | 8.24 ± 5.29* | 3.23 ± 0.49 | 10.04 ± 3.10** | 0.54 ± 0.21 | 2.39 ± 1.03** |
| 120 | 11.00 ± 10.50 | 7.20 ± 4.80 | 3.52 ± 0.63 | 7.42 ± 1.79** | 0.58 ± 0.39 | 1.43 ± 0.56** |
| 180 | 11.32 ± 13.30 | 7.15 ± 4.89 | 2.68 ± 0.37 | 4.79 ± 1.27** | 0.43 ± 0.28 | 0.54 ± 0.27 |
| 240 | 6.28 ± 4.64 | 2.95 ± 2.88 | 2.18 ± 0.23 | 3.61 ± 0.43** | 0.12 0.03 | 0.48 ± 0.19** |
| 300 | 1.57 (1.07 | 8.95 + 5.25** | 2.28 (0.09 | 3.37 (0.19** | 0.04 (0.01 | 0.38 (0.06** |
| 360 | 1.16 (0.31 | 7.08 (6.19* | 2.37 (0.41 | 2.68 (0.17 | 0.05 (0.05 | 0.26 (0.13** |

Note:
*t-test, p < 0.05;
**t-test, p < 0.01;

2.2.2 Duration of Gatifloxacin Ophthalmic Gel and Gatifloxacin Eyedrops in Corneas of Rabbit Eyes The results of the drug concentration of gatifloxacin ophthalmic gel and gatifloxacin eyedrops in corneas after single administration are shown in Table 5 and FIG. 2. The gatifloxacin ophthalmic gel group is sustained a relatively high drug concentration at the time of from 5 to 120 minute after administration, and the concentrations respectively are 25.91±6.30, 30.63±12.32, 23.87±7.37, 14.53±5.31, 10.25±2.69, 10.04±3.10 and 7.42±1.79 μg/g, which are respectively 1.9, 2.3, 3.2, 2.1, 2.0, 3.1 and 2.1 times of the gatifloxacin eyedrop group at the corresponding time points. The drug concentrations of the gatifloxacin ophthalmic gel group in corneas at respective time point of from 5 to 300 minute after administration are made a t-test over the gatifloxacin eyedrop group, and the results have significant differences (p<0.01). The area under the drug concentration in tears-time curve at the time of from 0 to 360 minute after administration is as follow: AUCGTX-Gel/AUCGTX-ED=2.1.

2.2.3 Duration of Gatifloxacin Ophthalmic Gel and Gatifloxacin Eyedrops in Aqueous Humor of Rabbit Eyes The results of the drug concentration of gatifloxacin ophthalmic gel and gatifloxacin eyedrops in aqueous humor after single administration are shown in Table 5 and FIG. 3. the drug concentration of the gatifloxacin ophthalmic gel group reaches peak concentration at 90 minute after administration, which is 2.39±1.03 μg/ml, while the drug concentration of the gatifloxacin eyedrop group reaches peak concentration at 60 in tears-time curve at the time of from 0 to 360 minute is as follow: AUCGTX-Gel/AUCGTX-ED=2.8.

2.2.4 Pharmacokinetic Parameters of Gatifloxacin Ophthalmic Gel and Gatifloxacin Eyedrop in Rabbit Eyes After Single Administration Drug concentration data of gatifloxacin ophthalmic gel and gatifloxacin eyedrop in tears, cornea and aqueous humor after single administration are fitted and calculated by a computer to obtain the corresponding pharmacokinetic parameters as shown in Table 6 (such as, DAS2.1.1 software can be used). The time at which the drug concentration of the gatifloxacin ophthalmic gel group reaches peak concentration is postponed. The areas under the drug concentrations in tears, cornea and aqueous humor-time curve of gatifloxacin ophthalmic gel group are respectively greater than the corresponding concentration of gatifloxacin eyedrop group.

TABLE 6

Pharmacokinetic parameters of test group and comparative group in rabbit eyes after single administration

| drug group | tissue | Cmax ($\bar{x} \pm s$ μg/g or ml) | Tmax min | $t^{1/2}$ min | Ka min-1 | AUC (μg/ml) * min |
|---|---|---|---|---|---|---|
| Comparative group | Tears | 2543.11 ± 2231.39 | 5 | 133.3 | — | 29274.94 |
| | Cornea | 13.56 ± 2.16 | 5 | 89.71 | — | 1388.52 |
| | Aqueous humor | 0.94 ± 0.69 | 60 | 59.8 | 0.0256 | 126.47 |

TABLE 6-continued

Pharmacokinetic parameters of test group and comparative group in rabbit eyes after single administration

| drug group | tissue | Cmax ($\bar{x} \pm s$ μg/g or ml) | Tmax min | $t^{1/2}$ min | Ka min-1 | AUC (μg/ml) * min |
|---|---|---|---|---|---|---|
| test group | Tears | 1864.85 ± 636.70 | 5 | 157.1 | — | 34313.07 |
| | Cornea | 30.63 ± 2.11 | 15 | 106.3 | — | 2893.61 |
| | Aqueous humor | 2.39 ± 1.03 | 90 | 72.5 | 0.0353 | 348.33 |

3. Conclusion

The results show that: by comparing the single administration of gatifloxacin ophthalmic gel to rabbit eyes with the administration of gatifloxacin eyedrops to rabbit eyes, it can be seen that the drug concentrations of gatifloxacin ophthalmic gel group in tears at 15 to 45 minute after administration are significantly greater than those of gatifloxacin eyedrop group, the drug concentrations of gatifloxacin ophthalmic gel group in cornea at 5 to 300 minute after administration are significantly greater than those of gatifloxacin eyedrop group, and the drug concentrations of gatifloxacin ophthalmic gel group in aqueous humor at 5 to 360 minute (except for 180 minute) after administration are significantly greater than those of gatifloxacin eyedrop group. The ocular bioavailability is significantly increased, and the results are shown in FIGS. 1 to 3.

TEST EXAMPLE 3

Comparison Among the Pharmacokinetics of Three Different Gatifloxacin Ophthalmic Gels The drug concentrations of three gatifloxacin ophthalmic gels prepared by different methods in cornea and aqueous humor at respective time points in a certain period after single administration to rabbit eyes are measured, and then the pharmacokinetics of the three formulations in rabbit eyes are compared.

1. Materials and Methods
1.1 Main Reagents

Acetonitrile (HPLC grade, batch number: 509124, TEDIA Inc. U.S.A.); methanol (HPLC grade, batch number: UN1230, Merck Inc. German); dichloromethane (chromatographic purity, Kemiou Chemical Reagent research institute of Tianjin). Gatifloxacin control sample (the content of 97.2%, China Biological Article Standardization Institute).

1.2 Test Drug

Group A: Gatifloxacin ophthalmic gel prepared according to the process of Example 5.
Group B: Gatifloxacin ophthalmic gel prepared according to the process of Comparative Example 1.
Group C: Gatifloxacin ophthalmic gel prepared according to the process of Comparative Example 2.

1.3 Animals and Grouping

Male Japanese white rabbits each is health, without ocular diseases, and has a weight of 2 to 2.5 kg (provided by Laboratory Animal Center of Henan Province, Certification No: SCXK(Yu)2005-0002). They are completely randomly grouped into three groups, i.e., group A, group B and group C, and each group includes 44 animals. The animals in each group are grouped into 11 subgroups, and each subgroup includes 4 animals with 8 eyes.

1.4 Administration and Sampling 0.050 g of gatifloxacin ophthalmic gel are accurately weighed by using clear glass eyedrop rod, and it is softly administrated to the bitamporal of conjunctival sac in the lower eyelid of the rabbit once, and then the two eyelids are closed softly for about 30 seconds. For each group, at 5, 15, 30, 45, 60, 90, 120, 180, 240, 300 and 360 minutes after administration, the anterior eye part is washed with physiological saline (not less than 10 ml for each eye). After the residual liquid is wiped out with dry tampon, a 1 ml syringe with a 26 gage injection needle is used to quickly stick into anterior chamber through the upper edge of the cornea to draw aqueous humor off. Aqueous humor is imbibed accurately to place into a test tube. Rabbits were sacrificed by excessive administration of pentobarbital sodium at the edge of rabbit ear, and the cornea tissues thereof are dissected out. The moisture of the obtained cornea tissue is blotted up with filter paper, and then the tissue is placed in a glass test tube to accurately weigh the weight thereof. All the samples are stored in a freezer at −60° C., and before the use, the frozen samples are thawed by returning the temperature to room temperature to be ready for treatment and determination.

1.5 Treatments to Samples

Aqueous humor: 100 μl of aqueous humor is accurately imbibed, and then 2.0 ml of dichloromethane is added, followed by swirl shaking (for 1 minute) and centrifugal separation (at 3000 rpm for 5 minutes). The upper aqueous layer is discarded, and the lower organic layer is collected. The obtained organic layer is blown dried with nitrogen gas by heating at 40° C. Before measurement, 100 μl of mobile phase is added to the dried organic layer with swirl shaking (at 4500 rpm for 1 minute) and centrifugal separation (for 15 minutes). The supernatant is separated to be added into a high pressure liquid chromatograph. By the calculation of external standard method of peak area, the concentration of the sample can be obtained.

Cornea sample: the cornea is weighed accurately, and after the weighed cornea is chopped, it is placed into a test tube, and then 1.0 ml of water is added. The mixture is homogenized by a tissue homogenizer (Fluko, German, at 25000 rpm for 1 minute). 200 μl of cornea homogenates are mixed with 2.0 ml of dichloromethane, and the other treating methods are the same as the treating methods for aqueous humor sample.

1.6 Determination for samples: the aqueous humor and cornea samples are respectively treated according to the methods in "the treatment to samples" item. The supernatant is separated to be infused into a high pressure liquid chromatograph, and the chromatogram and peak area are recorded. The concentrations of drugs in tears, aqueous humor and cornea samples are calculated by quantitation of external standard method.

2. Analyses for the Pharmacokinetics in Rabbit Eyes
2.1 Duration of Gatifloxacin in Cornea and Aqueous Humor The determined results of the drug concentration of three different gatifloxacin ophthalmic gels in cornea and aqueous humor of rabbit eyes after single administration are shown in FIGS. 4-5 and Table 7.

As shown in FIG. 4, after single topical administration to rabbit eyes, the time points at which the drug concentrations of group A, group B and group C in corneas of rabbit eyes reaches the peak value each are 15 minutes after administration, and the peak concentrations respectively are 36.28±8.86 μg/ml, 24.35±3.65 μg/ml, 21.69±6.37 μg/ml, wherein the peak concentration of group A is significantly greater than those of group B and group C.

As shown in FIG. 5, after administration to rabbit eyes, the time points at which the drug concentrations of group A, group B and group C in aqueous humor of rabbit eyes reaches the peak value each are 45 minutes, 45 minutes and 60 minutes respectively after administration, and the peak concentrations respectively are 3.33±0.93 µg/ml, 2.21±1.19 µg/ml, 2.38±0.65 µg/ml, wherein the peak concentration group A is significantly greater than those of group B and group C. The levels of the gatifloxacin concentration of respective group in aqueous humor are lower than those in cornea tissue, and the speeds of the adsorption and the elimination for drug concentration are also slower.

TABLE 7

Drug concentrations of gatifloxacin in cornea and aqueous humor of rabbit eyes

| Time (min) | concentration of gatifloxacin in cornea | | | Concentration of gatifloxacin in aqueous humor | | |
|---|---|---|---|---|---|---|
| | group A (µg/ml) ($\bar{x} \pm s$) | group B (µg/ml) ($\bar{x} \pm s$) | group C (g/ml) ($\bar{x} \pm s$) | group A ((g/ml) ($\bar{x} \pm s$) | group B (µg/ml) ($\bar{x} \pm s$) | group C (µg/ml) ($\bar{x} \pm s$) |
| 5 | 26.18 ± 7.57 | 10.37 ± 2.84 | 12.51 ± 3.26 | 0.27 ± 0.06 | 0.14 ± 0.04 | 0.09 ± 0.06 |
| 15 | 36.28 ± 8.86 | 24.35 ± 3.65 | 21.69 ± 6.37 | 0.38 ± 0.09 | 0.35 (0.12 | 0.27 (0.07 |
| 30 | 43.56 ± 6.15 | 19.21 ± 2.98 | 16.09 ± 4.21 | 1.92 ± 0.45 | 1.47 ± 0.31 | 0.53 ± 0.19 |
| 45 | 21.99 ± 5.52 | 12.87 ± 2.53 | 13.87 ± 3.76 | 3.33 ± 0.93 | 2.21 ± 1.19 | 1.68 ± 0.42 |
| 60 | 12.94 ± 3.85 | 10.97 ± 1.71 | 8.06 ± 2.32 | 2.12 ± 0.51 | 1.42 ± 0.82 | 2.38 ± 0.65 |
| 90 | 12.65 ± 3.78 | 7.52 ± 0.88 | 7.53 ± 1.72 | 2.55 ± 0.56 | 1.32 ± 1.02 | 1.12 ± 0.26 |
| 120 | 8.43 ± 2.39 | 4.62 ± 0.61 | 5.43 ± 1.40 | 1.43 ± 0.42 | 0.78 ± 0.33 | 0.77 ± 0.23 |
| 180 | 3.14 ± 1.35 | 3.56 ± 0.41 | 2.86 ± 0.65 | 0.58 ± 0.37 | 0.55 ± 0.23 | 0.69 ± 0.18 |
| 240 | 2.28 ± 0.25 | 2.09 ± 0.33 | 1.94 ± 0.23 | 0.38 ± 0.09 | 0.39 ± 0.13 | 0.34 ± 0.05 |
| 300 | 1.76 ± 0.10 | 1.97 ± 0.28 | 1.18 ± 0.54 | 0.28 ± 0.06 | 0.25 ± 0.11 | 0.17 ± 0.06 |
| 360 | 1.29 ± 0.41 | 1.12 ± 0.31 | 1.00 ± 0.68 | 0.16 ± 0.03 | 0.12 ± 0.08 | 0.08 ± 0.06 |

2.2.4 Pharmacokinetic Parameters of Gatifloxacin Ophthalmic Gel After Single Administration to Rabbit Eyes Drug concentration data of gatifloxacin ophthalmic gel in cornea and aqueous humor at respective time point after single administration are fitted by a computer, and then trapezoidal method, Wanger-Nelson method, and residual method are used to calculate corresponding pharmacokinetic parameters as shown in Table 8.

The area under drug concentration-time curve ($AUC_{0-360\ min}$) of group A in corneas is maximum, which is 2867.60 (µg/ml)*min, and is 1.36 times and 1.55 times of group B and group C respectively. This shows that the bioavailability of the formulation of group A in cornea is higher than other two groups.

The $AUC_{0-360\ min}$ of group A in aqueous humor is maximum, and this is consistent with the $AUC_{0-360\ min}$ of Group A in cornea. The $AUC_{0-360\ min}$ of Group A in aqueous humor is 353.3 (µg/ml)*min, and is 1.45 times and 1.51 times of group B and group C respectively. This shows that the bioavailability of the formulation of group A in cornea is higher than other two groups.

TABLE 8

Pharmacokinetic parameters of test group and comparative group in rabbit eyes after single administration

| drug group | Tissue | Cmax ($\bar{x} \pm s$ µg/g or ml) | Tmax min | t½ min | Ka min-1 | AUC (µg/ml) * min |
|---|---|---|---|---|---|---|
| group A | cornea | 36.28 ± 8.86 | 15 | 142.0 | 0.193 | 2867.60 |
| | aqueous humor | 3.33 ± 0.93 | 45 | 99.7 | 0.011 | 353.28 |
| group B | cornea | 24.35 ± 3.65 | 15 | 117.8 | 0.133 | 2109.48 |
| | aqueous humor | 2.21 ± 1.19 | 45 | 83.0 | 0.006 | 242.28 |
| group C | cornea | 21.69 ± 6.37 | 15 | 109.0 | 0.110 | 1854.68 |
| | aqueous humor | 2.38 ± 0.65 | 60 | 58.1 | 0.005 | 233.40 |

3. Conclusion

From the pharmacokinetic analyses results, it can be seen that in the peak concentrations of respective group in cornea, group A is maximum, and group B and group C are next, and thus in the bioavailability of respective group in cornea, group A is maximum, and group B and group C are next; in the peak concentrations of respective group in aqueous humor, group A is maximum, and group B and group C are next, and thus in the bioavailability of respective group in aqueous humor, group A is maximum, and group B and group C are next. The results show that: in the present study, after the topical administration in the same dosage and the same administering manner to rabbit eyes, as compared with the other two groups, the concentration of the gatifloxacin ophthalmic gel of group A is higher in cornea and aqueous humor of rabbit eyes during studying period, and the amount of the drug entering cornea and aqueous humor is most.

In the gatifloxacin ophthalmic gel prepared in the present invention, the combination of carbomer and sodium hyaluronate is used as gel matrix. The test results show that the peak concentrations and the bioavailabilities of the formulation in cornea and aqueous humor are significantly greater than the formulation of comparative group B (carbomer is used as gel matrix alone) and comparative group C (sodium hyaluronate is used as gel matrix alone).

Although specific embodiments of the present invention are herein illustrated and described in detail, the invention is not limited thereto. The above detailed descriptions are provided as exemplary of the present invention and should not be construed as constituting any limitation of the invention. Modifications will be obvious to those skilled in the art, and all modifications that do not depart from the spirit of the invention are intended to be included with the scope of the appended claims.

The invention claimed is:

1. An ophthalmic gel, in weight/volume percentage of the gel, comprising:

| | |
|---|---|
| gatifloxacin or its pharmaceutically acceptable salts | 0.1-2.0% |
| carbomer | 0.1-1.0% |
| sodium hyaluronate | 0.01-0.1% |
| water | q.s. to 100%. |

2. The ophthalmic gel according to claim 1, in weight/volume percentage of the gel, comprising:

| | |
|---|---|
| gatifloxacin or its pharmaceutically acceptable salts | 0.01-2.0% |
| carbomer | 0.05-4.0% |
| hydroxypropylmethylcellulose | 0.05-4.0% |
| sodium hyaluronate | 0.005-1.0% |
| water | q.s. to 100%. |

3. The ophthalmic gel according to claim 1 further comprising a pH regulator.

4. The ophthalmic gel according to claim 1 further comprising an osmotic regulator.

5. The ophthalmic gel according to claim 1 further comprising a bacteriostatic agent.

6. The ophthalmic gel according to claim 1 further comprising a surfactant.

7. The ophthalmic gel according to claim 3, wherein the pH regulator is selected from one or more of the group consisting of boric acid, borax, sodium hydroxide, phosphate buffered solution, and acetate buffered solution.

8. The ophthalmic gel according to claim 1, wherein the pH of the ophthalmic gel is 4.5 to 9.5.

9. The ophthalmic gel according to claim 4, wherein the osmotic regulator is selected from one or more of the group consisting of propylene glycol, glycerol, sodium chloride and mannitol.

10. The ophthalmic gel according to claim 4, wherein the ophthalmic gel comprises 0-15.0% (w/v) of the osmotic regulator.

11. The ophthalmic gel according to claim 5, wherein the bacteriostatic agent is selected from one or more of the group of phenethanol, phenoxyethanol, methylparaben, ethylparaben, propylparaben, benzalkonium chloride, chlorobutanol, benzalkonium bromide, and cetrimonium bromide.

12. The ophthalmic gel according to claim 5, wherein the bacteriostatic agent is present in an amount of 0.005 to 1% (w/v) based on the total weight of the gel.

13. The ophthalmic gel according to claim 6, wherein the surfactant is selected from one or more of the group consisting of tweens, polyoxyethylene hydrogenated castor oils, and polyoxyethylene castor oils.

14. The ophthalmic gel according to claim 6, wherein the surfactant is selected from one or more of the group consisting of tween-80, tween-60, tween-85, tween-65, and polyoxyethylene 60 hydrogenated castor oil.

15. The ophthalmic gel according to claim 6, wherein the ophthalmic gel comprises 0.01 to 10% (w/v) of the surfactant.

16. The ophthalmic gel according to claim 1, further comprising one or more surfactants selected from the group consisting of tweens, polyoxyethylene hydrogenated castor oils, and polyoxyethylene castor oils.

17. The ophthalmic gel according to claim 16, wherein the ophthalmic gel comprises 0.01 to 10% (w/v) of the surfactant.

* * * * *